(12) United States Patent
Hayashitani et al.

(10) Patent No.: US 12,283,370 B2
(45) Date of Patent: Apr. 22, 2025

(54) FACILITY PRESENTATION APPARATUS, FACILITY PRESENTATION METHOD AND RECORDING MEDIUM

(71) Applicants: NEC Corporation, Tokyo (JP); NEC Solution Innovators, Ltd., Tokyo (JP)

(72) Inventors: Masahiro Hayashitani, Tokyo (JP); Masahiro Kubo, Tokyo (JP); Akihiko Shibano, Tokyo (JP); Takayuki Banno, Tokyo (JP); Junichi Yahara, Tokyo (JP); Akira Yamauchi, Tokyo (JP); Hideyuki Taketa, Tokyo (JP); Kento Soma, Tokyo (JP)

(73) Assignees: NEC CORPORATION, Tokyo (JP); NEC Solution Innovators, Ltd., Tokyo (JP)

( * ) Notice: Subject to any disclaimer, the term of this patent is extended or adjusted under 35 U.S.C. 154(b) by 195 days.

(21) Appl. No.: 18/007,763

(22) PCT Filed: Apr. 22, 2021

(86) PCT No.: PCT/JP2021/016349
§ 371 (c)(1),
(2) Date: Dec. 2, 2022

(87) PCT Pub. No.: WO2021/246083
PCT Pub. Date: Dec. 9, 2021

(65) Prior Publication Data
US 2023/0230682 A1 Jul. 20, 2023

(30) Foreign Application Priority Data
Jun. 4, 2020 (JP) .................................. 2020-097593

(51) Int. Cl.
*G16H 40/20* (2018.01)
*G16H 10/60* (2018.01)

(52) U.S. Cl.
CPC ............. *G16H 40/20* (2018.01); *G16H 10/60* (2018.01)

(58) Field of Classification Search
CPC ................................ G16H 40/20; G16H 10/60
See application file for complete search history.

(56) References Cited

U.S. PATENT DOCUMENTS

| 10,708,795 B2 * | 7/2020 | Tapia ..................... H04W 24/04 |
| 2013/0204635 A1 * | 8/2013 | Okumura ............... G16H 40/20 |
| | | 705/2 |

(Continued)

FOREIGN PATENT DOCUMENTS

| JP | 2002-259571 A | 9/2002 |
| JP | 2007-172275 A | 7/2007 |

(Continued)

OTHER PUBLICATIONS

Sun-Jin Kim and Nae-Su Kim, "An approach about implementation and use of one-stop healthcare service system using RFID technology," 2006 8th International Conference Advanced Communication Technology, Phoenix Park, 2006, pp. 6 pp. -344, doi: 10.1109/ICACT.2006.205981. (Year: 2006).*

(Continued)

*Primary Examiner* — Sun M Li

(57) ABSTRACT

A facility presentation apparatus (1) includes: a selection unit (121) for selecting, as a recommended facility, at least one medical checkup facility recommended to a medical checkup target person from a plurality of medical checkup facilities based on a medical checkup information indicating a medical checkup that is related to a healthcare and that is intended to be taken by the medical checkup target person, a medical checkup facility information (1110) related to the plurality of medical checkup facilities in each of which the medical checkup can be performed and medical chart data (1220) of the medical checkup target person; and a presen- (Continued)

tation unit (122) for presenting, to a presentation target person, a recommended facility information related to the recommended facility.

9 Claims, 8 Drawing Sheets

(56) References Cited

U.S. PATENT DOCUMENTS

| | | | | |
|---|---|---|---|---|
| 2015/0133784 A1* | 5/2015 | Kapoor | ............... | A61B 8/5246 600/438 |
| 2019/0108914 A1* | 4/2019 | Chen | ....................... | A61B 5/002 |
| 2019/0189280 A1* | 6/2019 | Nagashima | ............ | G16H 50/20 |
| 2019/0392931 A1* | 12/2019 | Abousy | ................. | G16H 50/20 |
| 2020/0388362 A1* | 12/2020 | Blankinship | ........... | G16H 10/60 |
| 2021/0005324 A1* | 1/2021 | Bostic | .................... | G16H 50/20 |
| 2021/0174943 A1 | 6/2021 | Blanco | | |
| 2021/0176357 A1* | 6/2021 | Kirenko | ................ | G16H 30/20 |
| 2021/0391077 A1* | 12/2021 | Hirai | ................... | G06F 21/6245 |
| 2022/0383998 A1* | 12/2022 | Cossler | ................. | G16H 10/60 |

FOREIGN PATENT DOCUMENTS

| | | |
|---|---|---|
| JP | 2013-152632 A | 8/2013 |
| JP | 2017-142650 A | 8/2017 |
| JP | 2017-191362 A | 10/2017 |
| JP | 2018-005313 A | 1/2018 |
| JP | 2018-181136 A | 11/2018 |
| JP | 2019-517166 A | 6/2019 |
| JP | 2019-144746 A | 8/2019 |
| JP | 2020-016993 A | 1/2020 |
| JP | 2020-038715 A | 3/2020 |
| JP | 2021-093159 A | 6/2021 |
| JP | WO-2021246083 A1 * 12/2021 ............ G16H 10/60 |
| WO | 2012/124265 A1 | 9/2012 |

OTHER PUBLICATIONS

Boopala krishnan. N, Siva Sankara Sai. S and S. B. Mohanthy, "Real Time Internet Application with distributed flow environment for medical IoT," 2015 International Conference on Green Computing and Internet of Things , Greater Noida, India, 2015, pp. 832-837, doi: 10.1109/ICGCIoT.2015.7380578. (Year: 2015).*
S. Ravishankar, J. C. Ye and J. A. Fessler, "Image Reconstruction: From Sparsity to Data-Adaptive Methods and Machine Learning," in Proceedings of the IEEE, vol. 108, No. 1, pp. 86-109, Jan. 2020, doi: 10.1109/JPROC.2019.2936204. (Year: 2020) (Year: 2020).*
JP Office Action for JP Application No. 2022-528484, mailed on Jul. 2, 2024 with English Translation.
International Search Report for PCT Application No. PCT/JP2021/016349, mailed on Jun. 1, 2021.

* cited by examiner

1110

| LARGE ITEM | MIDDLE ITEM | CONTENT |
|---|---|---|
| FACILITY BASIC INFORMATION (1111) | FACILITY ID | ... |
| | FACILITY NAME | ... |
| | ADDRESS | ... |
| | ... | ... |
| FACILITY DETAIL INFORMATION #1 (1112) | MEDICAL CHECKUP ID | ... |
| | MEDICAL CHECKUP NAME | ... |
| | RESERVATION STATUS | ... |
| | RECORD | ... |
| | ... | ... |
| FACILITY DETAIL INFORMATION #2 (1112) | MEDICAL CHECKUP ID | ... |
| | MEDICAL CHECKUP NAME | ... |
| | RESERVATION STATUS | ... |
| | PERFORMANCE | ... |
| | ... | ... |
| ... | ... | ... |

| LARGE ITEM | MIDDLE ITEM | CONTENT |
|---|---|---|
| PATIENT BASIC INFORMATION | PATIENT ID | ... |
| | NAME | ... |
| | ADDRESS | ... |
| | BODY HEIGHT | ... |
| | BODY WEIGHT | ... |
| | PAST MEDICAL HISTORY | ... |
| | ... | ... |
| MEDICAL EXAMINATION HISTORY INFORMATION | CHIEF COMPLIANT | ... |
| | DETAIL OF MEDICAL CONSULTATION | ... |
| | TREATMENT POLICY | ... |
| | DETAIL OF TREATMENT | ... |
| | DETAIL OF MEDICINE | ... |
| | INSTRUCTION FROM DOCTOR | ... |
| | RESULT OF MEDICAL INTERVIEW | ... |
| | RESULT OF MEDICAL CHECKUP | ... |
| | ... | ... |

| RECOMMENDED MEDICAL CHECKUP | LARGE INTESTINE ENDOSCOPY | | DESIRED DAY | AFTER 4/1 | |
|---|---|---|---|---|---|

| FACILITY NAME | 4/1 | 4/2 | 4/3 | 4/4 | 4/5 | 4/6 |
|---|---|---|---|---|---|---|
| A HOSPITAL | × | × | × | × | × | 1 |
| B HOSPITAL | × | × | 2 | × | △ | △ |
| C CLINIC | △ | △ | ○ | ○ | ○ | ○ |
| D CLINIC | △ | 5 | △ | ○ | ○ | ○ |

AVAILABILITY: ○ : AVAILABLE, △ : AVAILABLE NUMBER IS SMALL, × : NOT AVAILABLE
NUMBER : DISPLAYED WHEN AVAILABLE NUMBER IS EQUAL TO OR SMALLER THAN 5

DO YOU ALLOW RECOMMENDED FACILITY TO USE MEDICAL CHART DATA ?   YES   NO

FIG. 14

FACILITY PRESENTATION APPARATUS, FACILITY PRESENTATION METHOD AND RECORDING MEDIUM

This application is a National Stage Entry of PCT/JP2021/016349 filed on Apr. 22, 2021, which claims priority from Japanese Patent Application 2020-097593 filed on Jun. 4, 2020, the contents of all of which are incorporated herein by reference, in their entirety.

TECHNICAL FIELD

This disclosure relates to a technical field of a facility presentation apparatus, a facility presentation method and a recording medium that are configured to select a medical checkup facility recommended to a medical checkup target person who wants to take a medical checkup and to present the selected medical checkup facility to a presentation target person.

BACKGROUND ART

It is desired that a medical checkup target person takes various medical checkups in a medical checkup facility for the purpose of a prevention or an early detection of a disease of the medical checkup target person. Therefore, an development of a technique for encouraging the medical checkup target person to take the medical checkup is desired. For example, a Patent Literature 1 discloses an apparatus that is configured to select a candidate of a visiting date for a health check based on a holiday and a custom in a country in which an expatriate lives and to notify the expatriate of the selected candidate of the visiting date, in order to make the expatriate take the health check.

Additionally, there is a Patent Literatures 2 to 5 as a background art document related to this disclosure.

CITATION LIST

Patent Literature

Patent Literature 1: JP2018-181136A
Patent Literature 2: WO2012/124265A
Patent Literature 3: JP2017-142650A
Patent Literature 4: JP2007-172275A
Patent Literature 5: JP2002-259571A

SUMMARY

Technical Problem

When there are a plurality of medical checkup facilities in each of which the medical checkup can be performed, it is desired that at least one proper test facility is selected as a recommended facility, which is recommended to the medical checkup target person, by considering a situation of each of the plurality of medical checkup facilities. However, the apparatus disclosed in the above described Patent Literature 1 does not consider whether or not there are the plurality of medical checkup facilities in each of which the medical checkup target person can take the medical checkup (the health check in the Patent Literature 1). Thus, the apparatus disclosed in the Patent Literature 1 has such a technical problem that the recommended facility, which is recommended to the medical checkup target person, is not necessarily selected properly.

It is an example object of this disclosure to provide a facility presentation apparatus, a facility presentation method and a recording medium that are configured to solve the above described technical problem. As one example, it is an example object of this disclosure to provide a facility presentation apparatus, a facility presentation method and a recording medium that are configured to properly select a recommended facility that is recommended to a medical checkup target person.

Solution to Problem

One example aspect of a facility presentation apparatus of this disclosure is includes: a selection unit that is configured to select, as a recommended facility, at least one medical checkup facility that is recommended to a medical checkup target person from a plurality of medical checkup facilities based on a medical checkup information indicating a medical checkup that is related to a healthcare and that is intended to be taken by the medical checkup target person, a medical checkup facility information related to the plurality of medical checkup facilities in each of which the medical checkup can be performed and medical chart data of the medical checkup target person; and a presentation unit that is configured to present, to a presentation target person, a recommended facility information related to the recommended facility.

One example aspect of a facility presentation method of this disclosure is includes: selecting, as a recommended facility, at least one medical checkup facility that is recommended to a medical checkup target person from a plurality of medical checkup facilities based on a medical checkup information indicating a medical checkup that is related to a healthcare and that is intended to be taken by the medical checkup target person, a medical checkup facility information related to the plurality of medical checkup facilities in each of which the medical checkup can be performed and medical chart data of the medical checkup target person; and presenting, to a presentation target person, a recommended facility information related to the recommended facility.

One example aspect of a recording medium of this disclosure is a recording medium on which a computer program that allows a computer to execute: a selection step at which at least one medical checkup facility that is recommended to a medical checkup target person is selected as a recommended facility from a plurality of medical checkup facilities based on a medical checkup information indicating a medical checkup that is related to a healthcare and that is intended to be taken by the medical checkup target person, a medical checkup facility information related to the plurality of medical checkup facilities in each of which the medical checkup can be performed and medical chart data of the medical checkup target person; and a presentation step at which a recommended facility information related to the recommended facility is presented to a presentation target person, is recorded.

Effect

The facility presentation apparatus, the facility presentation method and the recording medium described above are capable of to properly select the recommended facility that is recommended to the medical checkup target person.

BRIEF DESCRIPTION OF DRAWINGS

FIG. 14 illustrates one example of the recommended facility information that is presented to the presentation target person in the modified example.

DESCRIPTION OF EXAMPLE EMBODIMENTS

Next, an example embodiment of a facility presentation apparatus, a facility presentation method and a recording medium will be described with reference to the drawings. In the below described description, a facility presentation system SYS to which the example embodiment of the facility presentation apparatus, the facility presentation method and the recording medium is applied will be described. The facility presentation system SYS may be used in a healthcare institution where a healthcare service is provided to a patient, for example. The healthcare institution may include at least one of a hospital, a health clinic, a long-term care health facility, a dispensing pharmacy and any facility that provides the healthcare service (for example, at least one of a facility that provides a health check and a facility that provides any clinical test), for example.

(1) Configuration of Facility Presentation System SYS

Firstly, a configuration of the facility presentation system SYS will be described.

(1-1) Entire Configuration of Facility Presentation System SYS

Figure 1:
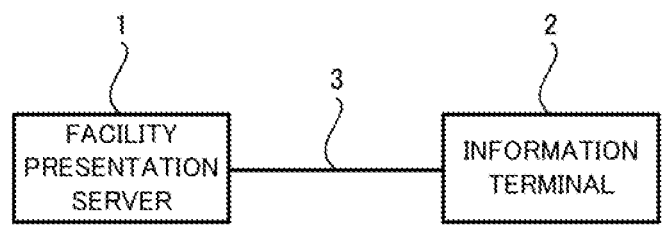
FIG. 1 is a block diagram that illustrates an entire configuration of a facility presentation system in a present example embodiment.

Firstly, with reference to FIG. 1, an entire configuration of the facility presentation system SYS in the present example embodiment will be described. FIG. 1 is a block diagram that illustrates the entire configuration of the facility presentation system SYS in the present example embodiment.

The facility presentation system SYS is configured to select, as a recommended facility, at least one medical checkup facility that is recommended to a medical checkup target person and to present, to a presentation target person, an recommended facility information related to the selected recommended facility, when the medical checkup target person intends to take a medical checkup (namely, has a schedule to take the medical checkup). The facility presentation system SYS may propose that the presentation target person should take the medical checkup in the recommended facility by presenting the recommended facility information to the presentation target person. The medical checkup which the medical checkup target person intends to take may include at least one of a medical checkup which the medical checkup target person wants to take, a medical checkup which the medical checkup target person is recommended to take and a medical checkup which the medical checkup target person should take. In the below described description, the medical checkup which the medical checkup target person intends to take is referred to as a "recommended medical checkup" for the purpose of description. The "medical checkup target person" in the present example embodiment is any person who intends to take the recommended medical checkup. The medical checkup target person may include a patient who has taken a medical examination in the healthcare institution that uses the facility presentation system SYS, for example. The medical checkup target person may include a patient who is recommended to take the recommended medical checkup in the healthcare institution that uses the facility presentation system SYS, for example. Moreover, the "medical checkup" in the present example embodiment includes any medical checkup (for example, a clinical test) related to a healthcare. The clinical test may include a physiological test (in other words, a physiological function test) that directly tests a body of the medical checkup target person, and may include an antibody test that tests a sample (namely, a specimen material) collected from the body of the test target person. Moreover, the "medical checkup facility" in the present example embodiment is any facility in which the above described medical checkup can be performed. The above described healthcare institution (for example, at least one of the hospital, the health clinic, the long-term care health facility, the dispensing pharmacy and any facility that provides the healthcare service (for example, at least one of the facility that provides the health check and the facility that provides any clinical test)) is one example of the medical checkup facility. Moreover, the "presentation target person" in the present example embodiment is any person to whom the recommended facility information is presented. The presentation target person may be a person who is same as the medical checkup target person. The presentation target person may be a person (for example, a healthcare worker) who is different from the medical checkup target person. Note that the "healthcare worker" in the present example embodiment is a person in general engaged in a healthcare, which is an activity for the purpose of at least one of a treatment of a disease, a prevention of the disease, a maintenance of a health, a restoration of a health, and an improvement of a health. The healthcare worker may include at least one person of a doctor, a dentist, a healthcare professional (for example, at least one person of a nurse, a pharmacist, a clinical laboratory technician, a radiology technician, a physical therapist and so on) and so on.

In order to select the recommended facility and present the recommended facility information indicating the selected recommended facility to the presentation target person, the facility presentation system SYS includes a facility presentation server 1 that is one specific example of "a facility presentation apparatus" and an information terminal 2, as illustrated in FIG. 1. The facility presentation server 1 and the information terminal 2 are configured to communicate with each other through a communication network 3. The communication network 3 may include a wired communication network and may include a wireless communication network.

The facility presentation server 1 is an information processing apparatus that is usable by the healthcare institution that uses the facility presentation system SYS. Thus, the facility presentation server 1 is typically placed for the healthcare institution. In this case, the facility presentation server 1 may be placed inside the healthcare institution (for example, inside a healthcare facility of the healthcare institution), and may be placed outside the healthcare institution (for example, a facility placed outside the healthcare facility of the healthcare institution). The facility presentation server 1 is configured to perform a facility presentation operation. Specifically, the facility presentation server 1 may perform, as a part of the facility presentation operation, an operation for selecting the recommended facility. Furthermore, the facility presentation server 1 may perform, as another part of the facility presentation operation, an operation for presenting the recommended facility information to the presentation target person by using the information terminal 2 that is configured to present any information to the presentation target person. Namely, the facility presentation server 1 may perform, as another part of the facility presentation operation, an operation for controlling the information terminal 2 to present the recommended facility information to the presentation target person.

The information terminal 2 is an information processing apparatus that is usable by the presentation target person. An information processing apparatus (for example, at least one of a personal computer and a tablet terminal) that is placed for the healthcare institution may be used as the information terminal 2. An information processing apparatus (for example, at least one of a personal computer, a tablet terminal and a smartphone) of the presentation target person may be used as the information terminal 2. The information terminal 2 is configured to present the recommended facility information to the presentation target person under the control of the facility presentation server 1, as described above. As a result, the presentation target person can recognize the recommended facility. Namely, the presentation target person can recognize which medical checkup facility the medical checkup target person is recommended (in other words, suggested or proposed) to take the recommended medical checkup.

(1-2) Configuration of Facility Presentation Server 1

Figure 2:
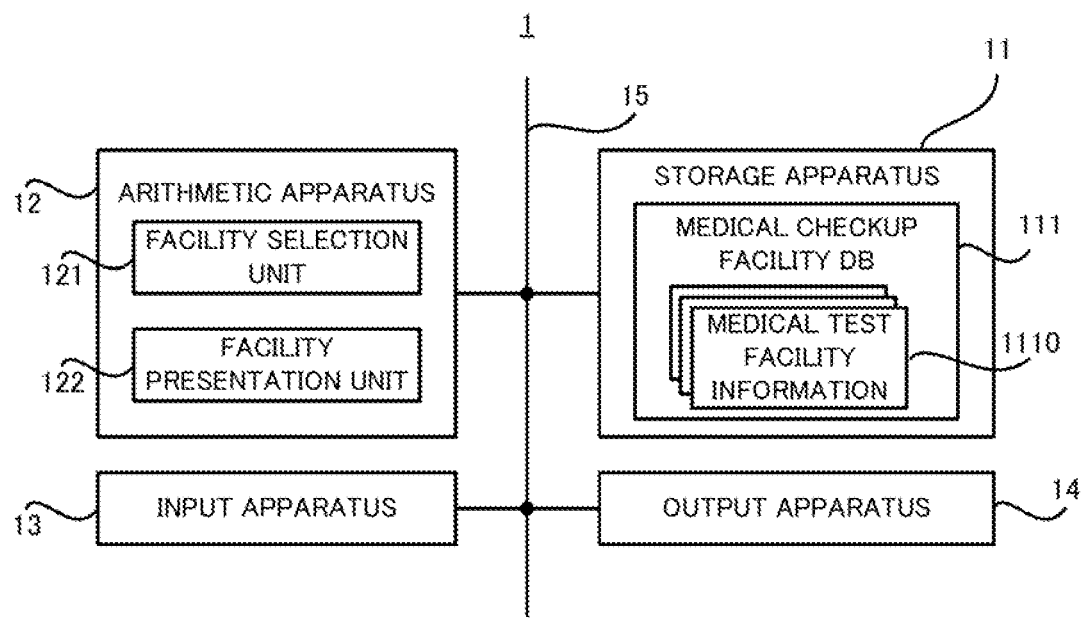
FIG. 2 is a block diagram that illustrates a configuration of a facility presentation server in the present example embodiment.

Next, with reference to FIG. 2, a configuration of the facility presentation server 1 will be described. FIG. 2 is a block diagram that illustrates the configuration of the facility presentation server 1.

As illustrated in FIG. 2, the facility presentation server 1 includes a storage apparatus 11 and an arithmetic apparatus 12. Furthermore, the facility presentation server 1 may include an input apparatus 13 and an output apparatus 14. However, the facility presentation server 1 may not include at least one of the input apparatus 13 and the output apparatus 14. The storage apparatus 11, arithmetic apparatus 12, the input apparatus 13 and the output apparatus 14 may be interconnected through a data bus 15.

The storage apparatus 11 is configured to store desired data. For example, the storage apparatus 11 may temporarily store the computer program that is executed by the arithmetic apparatus 12. The storage apparatus 11 may temporarily store data temporarily used by the arithmetic apparatus 12 when the arithmetic apparatus 12 executes the computer program. The storage apparatus 11 may store data stored for a long term by the facility presentation server 1. The storage apparatus 11 may include at least one of a RAM (Random Access Memory), a ROM (Read Only Memory), a hard disk apparatus, a magneto-optical disc, a SSD (Solid State Drive) and a disk array apparatus. Namely, the storage apparatus 11 may include a non-transitory recording medium.

In the present example embodiment, the storage apparatus 11 stores data used by the facility presentation server 1 to select the recommended facility. FIG. 2 illustrates a medical checkup facility DB (Database) 111 as one example of the data used by the facility presentation server 1 to select the recommended facility. Namely, FIG. 2 illustrates an example in which the storage apparatus 11 stores the medical checkup facility DB 111.

The medical checkup facility DB 111 is a database that stores an medical checkup facility information 1110 including an information relate to the medical checkup facility. Generally, there are a plurality of medical checkup facilities in each of which the medical checkup can be performed. For example, there may be a plurality of medical checkup facilities each of which a same type of the medical checkup can be performed. For example, there may be a plurality of medical checkup facilities in which a different types of the medical checkups can be performed, respectively. Thus, the medical checkup facility DB 111 stores a plurality of medical checkup facilities information 1110 that correspond to the plurality of medical checkup facilities, respectively. Each medical checkup facility information 1110 includes an information related to one medical checkup facility corresponding to each medical checkup facility information 1110.

Figures 3, 4:
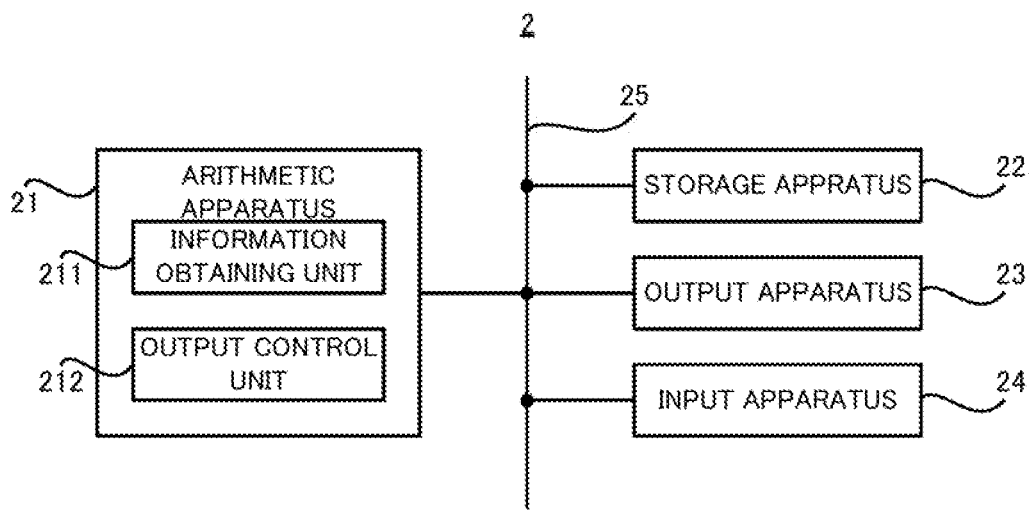
FIG. 3 is a data structure diagram that illustrates one example of a data structure of facility data.
FIG. 4 is a block diagram that illustrates a configuration of an information terminal in the present example embodiment.

FIG. 3 illustrates one example of the medical checkup facility information 1110. As illustrated in FIG. 3, the medical checkup facility information 1110 may include a facility basic information 1111 and a facility detail information 1112.

The facility basic information 1111 includes a basic information for identifying the medical checkup facility. For example, in an example illustrated in FIG. 3, the facility basic information 1111 includes a facility ID for identifying the medical checkup facility, an information related to a name of the medical checkup facility (a facility name) and an information related to an address of the medical checkup facility. However, the facility basic information 1111 may not include at least one of plurality of these information. The facility basic information 1111 may include other information in addition to or instead of at least one of the plurality of information illustrated in FIG. 3.

The facility detail information 1112 includes a detail information related to the medical checkup that can be performed in the medical checkup facility (in the below described description, it is referred to as "a feasible medical checkup"). For example, the facility detail information 1112 may include an information indicating the feasible medical checkup. In the example illustrated in FIG. 3, the facility detail information 1112 includes, as the information indicating the feasible medical checkup, a medical checkup ID for identifying the feasible medical checkup and an information related to a name of the feasible medical checkup (a medical checkup name). Furthermore, the facility detail information 1112 may include an information related to a feasibility of the feasible medical checkup. For example, in the example illustrated in FIG. 3, the facility detail information 1112 includes, as the information related to the feasibility of the feasible medical checkup, an information related to a reservation status of the feasible medical checkup in the medical checkup facility and an information related to a performance of the feasible medical checkup that has been performed in the medical checkup facility. The information related to the reservation status of the feasible medical checkup may include at least one of an information related to a date and time on which the feasible medical checkup is reserved, an information related to the number of the feasible medical checkup that has been already reserved in a certain date and time, an information related to a date and time on which the feasible medical checkup can be reserved and an information related to the number of a new reservation that can be accepted for the feasible medical checkup in a certain date and time (namely, the number of vacancy of the reservation of the feasible medical checkup), for example. Note that the medical checkup facility generally provides the feasible medical checkup by using a medical checkup apparatus. Thus, a total sum of the number of the feasible medical checkup that has been already reserved in a certain date and time and the number of the new reservation that can be still accepted for the feasible medical checkup in the same date and time is typically equal to or smaller than a total number of the medical checkup apparatus for providing the feasible medical checkup. Moreover, the information related to the performance of the feasible medical checkup that has been performed in the medical checkup facility may include at least one of an information related to the number of times by which the feasible medical checkup has been performed in the medical checkup facility and an information related to an evaluation (what we call a word of mouth) relative to the feasible medical checkup from a person who has taken the feasible medical checkup in the medical checkup facility, for example. However, the facility detail information 1112 may not include at least one of plurality of these information. The facility detail information 1112 may include other information in addition to or instead of at least one of the plurality of information illustrated in FIG. 3.

The different types of the feasible medical checkups can be performed in the medical checkup facility in some cases. In this case, the medical checkup facility information 1110 may include a plurality of facility detail information 1112 corresponding to the different types of the feasible medical checkups, respectively, that can be performed in the medical checkup facility. For example, the medical checkup facility information 1110 may include a first facility detail information 1112 including a detailed information related to a first type of feasible medical checkup and a second facility detail information 1112 including a detailed information related to a second type of feasible medical checkup that is different from the first type of feasible medical checkup.

Again in FIG. 2, the arithmetic apparatus 12 includes a CPU (Central Processing Unit), for example. The arithmetic apparatus 12 reads a computer program. For example, the arithmetic apparatus 12 may read a computer program stored in the storage apparatus 11. For example, the arithmetic apparatus 12 may read a computer program stored in a computer-readable and non-transitory recording medium, by using a not-illustrated recording medium reading apparatus. The arithmetic apparatus 12 may obtain (namely, download or read) a computer program from a not-illustrated apparatus placed outside the facility presentation server 1 through a not-illustrated communication apparatus. The arithmetic apparatus 12 executes the read computer program. As a result, a logical functional block for performing an operation (for example, the above described facility presentation operation) that should be performed by the facility presentation server 1 is implemented in the arithmetic apparatus 12. Namely, the arithmetic apparatus 12 is configured to serve as a controller for implementing the logical block for performing the operation that should be performed by the facility presentation server 1.

FIG. 2 illustrates one example of the logical block that is implemented in the arithmetic apparatus 12 to perform the facility presentation operation. As illustrated in FIG. 2, a facility selection unit 121 that is one specific example of "a selection unit" and a facility presentation unit 122 that is one specific example of "a presentation unit" are implemented in the arithmetic apparatus 12. Note that a detail of the operation performed by the facility selection unit 121 and the facility presentation unit 122 will be described later in detail, however, an overview thereof is briefly described here. The facility selection unit 121 is configured to select the recommended facility based on the medical checkup facility DB 111. The facility presentation unit 122 is configured to control the information terminal 2 to present, to the presentation target, the recommended facility information related to the recommended facility selected by the facility selection unit 121.

The input apparatus 13 is an apparatus that is configured to receive an input of an information from an outside of the facility presentation server 1 to the facility presentation server 1.

The output apparatus 14 is an apparatus that is configured to output an information to an outside of the facility presentation server 1. For example, the output apparatus 14 may output an information related to the facility presentation operation performed by the facility presentation server 1. For example, the output apparatus 14 may output (namely, transmit), to the information terminal 2 through the communication network 3, a control information for controlling the information terminal 2 to present the recommended facility information.

(1-3) Configuration of Information Terminal 2

Next, with reference to FIG. 4, a configuration of the information terminal 2 will be described. FIG. 4 is a block diagram that illustrates the configuration of the information terminal 2.

As illustrated in FIG. 4, the information terminal 2 includes a storage apparatus 21, an arithmetic apparatus 22 and an output apparatus 23. Furthermore, the information terminal 2 may include an input apparatus 24. However, the information terminal 2 may not include the input apparatus 24. The storage apparatus 21, arithmetic apparatus 22, the output apparatus 23 and the input apparatus 24 may be interconnected through a data bus 25.

The storage apparatus 21 is configured to store desired data. For example, the storage apparatus 21 may temporarily store the computer program that is executed by the arithmetic apparatus 22. The storage apparatus 21 may temporarily store data temporarily used by the arithmetic apparatus 22 when the arithmetic apparatus 22 executes the computer program. The storage apparatus 21 may store data stored for a long term by the information terminal 2. The storage apparatus 21 may include at least one of a RAM, a ROM, a hard disk apparatus, a magneto-optical disc, a SSD and a disk array apparatus. Namely, the storage apparatus 21 may include a non-transitory recording medium.

The arithmetic apparatus 22 includes a CPU, for example. The arithmetic apparatus 22 reads a computer program. For example, the arithmetic apparatus 22 may read a computer program stored in the storage apparatus 21. For example, the arithmetic apparatus 22 may read a computer program stored in a computer-readable and non-transitory recording medium, by using a not-illustrated recording medium reading apparatus. The arithmetic apparatus 22 may obtain (namely, download or read) a computer program from a not-illustrated apparatus placed outside the information terminal 2 through a not-illustrated communication apparatus. The arithmetic apparatus 22 executes the read computer program. As a result, a logical functional block for performing an operation that should be performed by the information terminal 2 is implemented in the arithmetic apparatus 22. Namely, the arithmetic apparatus 22 is configured to serve as a controller for implementing the logical block for performing the operation that should be performed by the information terminal 2.

In the present example embodiment, the information terminal 2 is configured to perform a recommended facility information output operation for outputting the recommended facility information in a form that allows the presentation target person to recognize it, under the control the facility presentation server 1. FIG. 4 illustrates one example of the logical block that is implemented in the arithmetic apparatus 22 to perform the recommended facility information output operation. As illustrated in FIG. 4, an information obtaining unit 221 and an output control unit 222 are implemented in the arithmetic apparatus 22. The information obtaining unit 221 is configured to obtain the control information for controlling the information terminal 2 to present the recommended facility information. The output control unit 222 is configured to control, based on the control information obtained by the information obtaining unit 221, the output apparatus 23 to output recommended facility information in a form that allows the presentation target person to recognize it.

The output apparatus 23 is an apparatus that is configured to output an information to an outside of the information terminal 2. For example, the output apparatus 23 may output an image. Namely, the output apparatus 23 may include a display apparatus (what we call a display) that is configured to display the image. In this case, the output apparatus 23 may present the recommended facility information to the presentation target person by displaying the recommended facility information as the image. As a result, the presentation target person can recognize the recommended facility information by using a visual sense. For example, the output apparatus 23 may output a sound. Namely, the output apparatus 23 may include a sound apparatus (what we call a speaker) that is configured to output the sound. In this case, the output apparatus 23 may present the recommended facility information to the presentation target person by outputting the recommended facility information as the sound. As a result, the presentation target person can recognize the recommended facility information by using a hearing sense. For example, the output apparatus 23 may output the information on a paper. Namely, the output apparatus 23 may include a print apparatus (what we call a printer) that is configured to print a desired information on the paper. In this case, the output apparatus 23 may present the recommended facility information to the presentation target person by printing the recommended facility information on the paper. As a result, the presentation target person can recognize the recommended facility information by using the visual sense.

The input apparatus 24 is an apparatus that is configured to receive an input of an information from an outside of the information terminal 2 to the information terminal 2.

The information terminal 2 may be placed on a traffic line of the presentation target person in the healthcare institution for which the facility presentation server 1 is placed. For example, when the presentation target person is the medical checkup target person (for example, the patient) as described above, the information terminal 2 may be placed on the traffic line of the patient in the healthcare institution. The traffic line of the patient in the healthcare institution may include a traffic line between a reception, a waiting room and a medical consultation room in the healthcare institution. As one example, the information terminal 2 may be placed at the reception of the healthcare institution (for example, a place where the patient who has finished taking the medical examination pays a healthcare expenditure). In this case, the patient can recognize the recommended facility, in which he can take the recommended medical checkup that is recommended to take by the healthcare worker in the medical examination, at a timing when he pays the healthcare expenditure after taking the medical examination in the healthcare examination. As another example, the information terminal 2 may be placed in the waiting room of the healthcare institution (for example, a place where the patient wait for the medical examination or the payment of the healthcare expenditure). In this case, the patient can recognize the recommended facility, in which he can take the recommended medical checkup that is recommended to take by the healthcare worker in the medical examination, at a timing when he waits for the payment of the healthcare expenditure after taking the medical examination in the healthcare examination. For example, when the presentation target person is the healthcare worker as described above, the information terminal 2 may be placed in a room where the medical examination is performed (for example, the medical consultation room). In this case, the healthcare worker can recognize the recommended facility while performing the medical examination for the patient (namely, the medical checkup target person). As a result, the healthcare worker can inform the patient of the recommended facility while performing the medical examination for the patient (namely, the medical checkup target person).

Alternatively, when the information processing apparatus of the medical checkup target person is used as the information terminal 2 as described above, the medical checkup target person can recognize the recommended facility 8 at a desired place (for example, a home of the medical checkup target person and the like) without vising the healthcare institution.

(2) Facility Presentation Operation Performed by Facility Presentation Server 1

Figure 5:
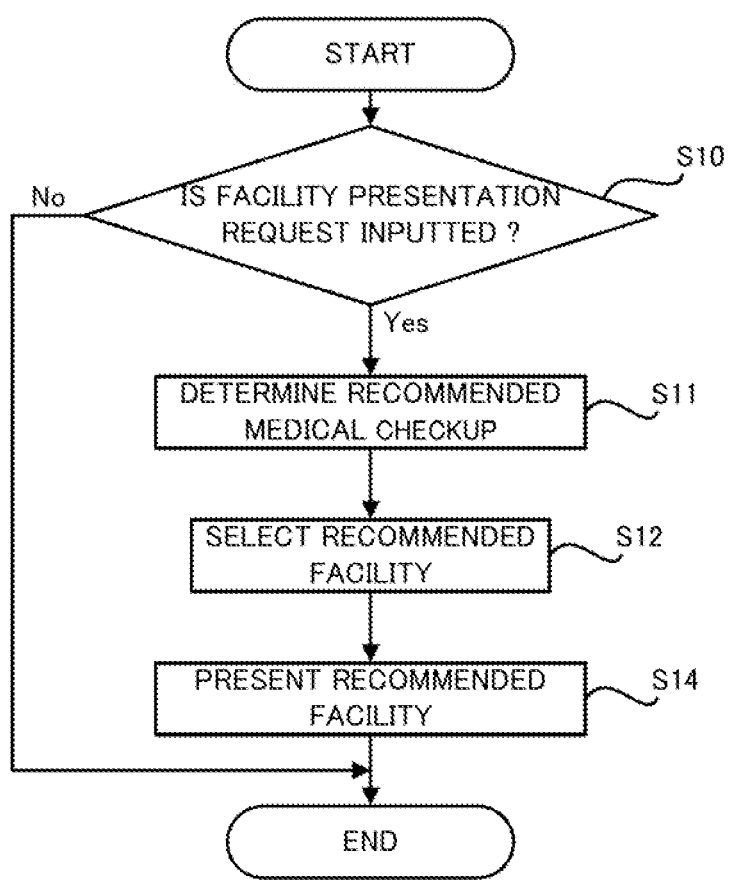
FIG. 5 is a flow chart that illustrates a flow of a facility presentation operation performed by the facility presentation server.

Next, with reference to FIG. 5, the facility presentation operation performed by the facility presentation server 1 will be described. FIG. 5 is a flowchart that illustrates the facility presentation operation performed by the facility presentation server 1.

As illustrated in FIG. 5, firstly, the facility selection unit 121 determines whether or not the facility presentation request, which is to request the facility presentation server 1 to perform the facility presentation operation, is inputted into the facility presentation server 1 (a step S10). The facility presentation request may be inputted into the facility presentation server 1 by at least one of the presentation target person and the medical checkup target person. For example, when the presentation target person is same as the medical checkup target person, the presentation target person (namely, the medical checkup target person) may transmit (namely, input) the facility test presentation request to the facility presentation server 1 by using the input apparatus 24 of the information terminal 2. For example, when the presentation target person is a person (for example, the healthcare worker) who is different from the medical checkup target person, the presentation target person (for example, the healthcare worker) may transmit (namely, input) the facility presentation request to the facility presentation server 1 by using the input apparatus 13 of the facility presentation server 1.

As a result of the determination at the step S10, when it is determined that the facility presentation request is not inputted (the step S10: No), the facility presentation server 1 may end the facility presentation operation illustrated in FIG. 5. After ending the facility presentation operation, the facility presentation server 1 may star the facility presentation operation again after a predetermined time elapses.

On the other hand, as a result of the determination at the step S10, when it is determined that the facility presentation request is inputted (the step S10: Yes), the facility selection unit 121 selects the recommended facility (a step S11 to a step S12). Specifically, the facility selection unit 121 firstly determines, based on an information included in the facility presentation request, the recommended medical checkup which the medical checkup target person wants to take (the step S11). Thus, it is preferable that the facility presentation request include a recommended medical checkup information including an information indicating the recommended medical checkup which the medical checkup target person wants to take. Alternatively, the facility selection unit 121 may obtain the recommended medical checkup information separately from the facility presentation request. Then, the facility selection unit 121 selects, based on the medical checkup facility DB 111 stored in the storage apparatus 11, the recommended facility in which the medical checkup target person is recommended to take the recommended medical checkup determined at the step S11 (the step S12). Namely, the facility selection unit 121 selects, as the recommended facility, at least one medical checkup facility that is recommended to the medical checkup target person who wants to take the recommended medical checkup determined at the step S11 from the plurality of medical checkup facilities corresponding to the plurality of medical checkup facility information 1110, respectively, stored in the medical checkup facility DB 111, based on the recommended medical checkup information included in the facility presentation request and the medical checkup facility DB 111 stored in the storage apparatus 11 (the step S12).

For example, the facility selection unit 121 may extract, from the medical checkup facility DB 111, the medical checkup facility information 1110 corresponding to the medical checkup facility in which the recommended medical checkup determined at the step S11 can be performed. Then, the facility selection unit 121 may determine based on the facility detail information 1112 (especially, the information related to the reservation status of the medical checkup facility) included in the extracted medical checkup facility information 1110 whether or not the new reservation for the recommended medical checkup is still acceptable by the *medica* test facility corresponding to the extracted medical checkup facility information 1110. As a result, the facility selection unit 121 may select, as the recommended facility, the medical checkup facility that is capable of still accepting the new reservation for the recommended medical checkup (in the below described description, it is referred to as a "reservation-ready medical checkup facility"). In this case, the facility selection unit 121 may select the recommended facility by using a selection engine that is configured to output the recommended facility by searching the plurality of medical checkup facility information 1110 based on the recommended facility information when the recommended facility information is inputted thereto. The selection engine may be a rule-based engine.

When there are a plurality of reservation-ready medical checkup facilities, the facility selection unit 121 may select each of at least two of the plurality of reservation-ready medical checkup facilities as the recommended facility. Namely, the facility selection unit 121 may select a plurality of recommended facilities.

When there are a plurality of reservation-ready medical checkup facilities, the facility selection unit 121 may select all of the plurality of reservation-ready medical checkup facilities as the recommended facilities. Namely, the facility selection unit 121 may select, as the recommended facility, the reservation-ready medical checkup facility unconditionally.

Figure 6:
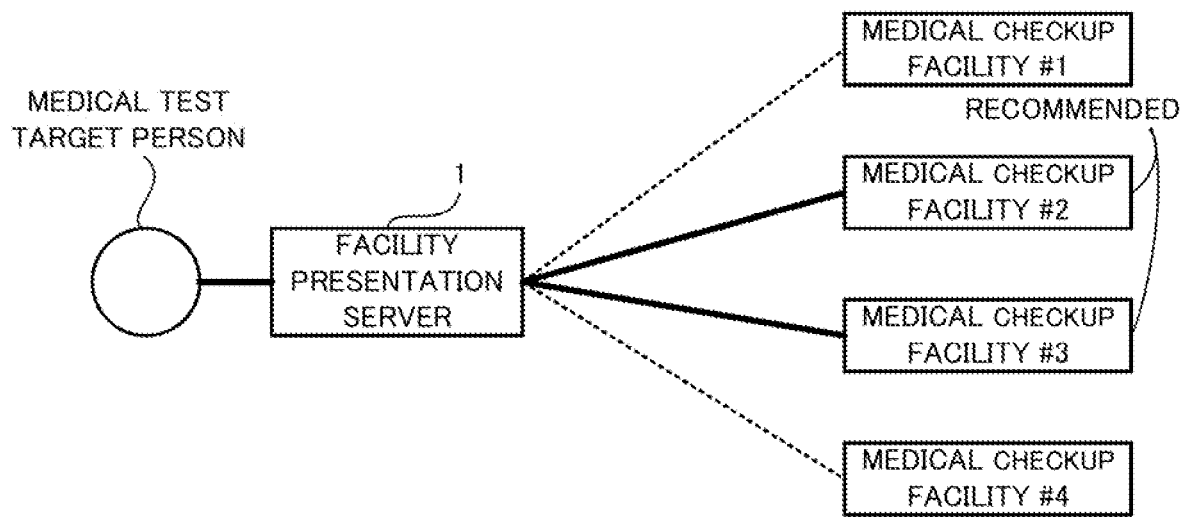
FIG. 6 conceptionally illustrates an operation for selecting a recommended facility.

Alternatively, the facility selection unit 121 may select only a part of the plurality of reservation-ready medical checkup facilities as the recommended facility. The facility selection unit 121 may not select another part of the plurality of reservation-ready medical checkup facilities as the recommended facility. Specifically, the facility selection unit 121 may select a part of the plurality of reservation-ready medical checkup facilities as the recommended facility and may not select another part of the plurality of reservation-ready medical checkup facilities as the recommended facility, based on a desired facility selection rule. For example, FIG. 6 conceptionally illustrate a situation where medical checkup facilities #2 and #3 are selected as the recommended medical checkup facilities and medical checkup facilities #1 and #4 are not selected as the recommended medical checkup facilities when the four medical checkup facilities #1 to #4 are the reservation-ready medical checkup facilities.

The facility selection rule may include such a first rule that the medical checkup facility that is affiliated with (namely, that has same affiliation with) one healthcare institution that uses the facility presentation system SYS is more likely to be selected as the recommended facility than the medical checkup facility that is not affiliated with the one healthcare institution. When the first rule is used, the facility basic information 1111 included in the medical checkup facility information 1110 may include an information related to the healthcare institution that is affiliated with the medical checkup facility. As a result, the facility selection unit 121 is capable of selecting the recommended facility based on the medical checkup facility information 1110 so that the first rule is satisfied. In this case, the facility selection unit 121 is capable of preferentially selecting, as the recommended facility, the medical checkup facility that is affiliated with the one healthcare institution. As a result, the one healthcare institution using the facility presentation system SYS is capable of preferentially using a resource of the medical checkup facility that is affiliated with the one healthcare institution. Namely, the one healthcare institution using the facility presentation system SYS is capable of effectively using the resource of the medical checkup facility that is affiliated with the one healthcare institution.

The facility selection rule may include such a second rule that the medical checkup facility in which the performance of the medical checkup the type of which is same as the recommended medical checkup is relatively high is more likely to be selected as the recommended facility than the medical checkup facility in which the performance of the medical checkup the type of which is same as the recommended medical checkup is relatively low. For example, the second rule may include such a rule that the medical checkup facility in which the medical checkup the type of which is same as the recommended medical checkup has been performed by a relatively large number of times is more likely to be selected as the recommended facility than the medical checkup facility in which the medical checkup the type of which is same as the recommended medical checkup has been performed by a relatively small number of times. For example, the second rule may include such a rule that the medical checkup facility in which the evaluation (the word of mouth) relative to the medical checkup the type of which is same as the recommended medical checkup is relatively high is more likely to be selected as the recommended facility than the medical checkup facility in which the evaluation relative to the medical checkup the type of which is same as the recommended medical checkup is relatively low. As described above, the facility detail information 1112 included in the medical checkup facility information 1110 includes the information related to the performance of the medical checkup that has been performed in the medical checkup facility. Thus, the facility selection unit 121 is capable of selecting the recommended facility based on the medical checkup facility information 1110 so that the second rule is satisfied. In this case, the facility selection unit 121 is capable of preferentially selecting, as the recommended facility, the medical checkup facility having the relatively high performance. As a result, the medical checkup target person can take the recommended medical checkup in the medical checkup facility having the relatively high performance.

The facility selection rule may include such a third rule that the medical checkup facility in which the number of the reservation for the medical checkup the type of which is same as the recommended medical checkup (namely, the number of the medical checkup that has been reserved) is relatively small is more likely to be selected as the recommended facility than the medical checkup facility in which the number of the reservation for the medical checkup the type of which is same as the recommended medical checkup is relatively large. In other words, the facility selection rule may include such a third rule that the medical checkup facility in which the number of the new reservation that can be still accepted for the medical checkup the type of which is same as the recommended medical checkup (namely, the number of the available reservation for the medical checkup the type of which is same as the recommended medical checkup) is relatively large is more likely to be selected as the recommended facility than the medical checkup facility in which the number of the new reservation that can be still accepted for the medical checkup the type of which is same as the recommended medical checkup is relatively small. As described above, the facility detail information 1112 included in the medical checkup facility information 1110 includes the information related to the reservation status of the medical checkup that can be performed in the medical checkup facility. Thus, the facility selection unit 121 is capable of selecting the recommended facility based on the medical checkup facility information 1110 so that the third rule is satisfied. In this case, the facility selection unit 121 is capable of preferentially selecting, as the recommended facility, the medical checkup facility in which the number of the available reservation is relatively large. Thus, there is a low possibility that the facility selection unit 121 is less likely to biasedly select only a certain medical checkup facility as the recommended facility. Namely, there is a low possibility that the facility selection unit 121 selects the plurality of medical checkup facilities about evenly. As a result, the resources of the plurality of medical checkup facilities are used about evenly. Namely, the resources of the plurality of medical checkup facilities are used effectively.

The facility selection rule may include such a fourth rule that the medical checkup facility that is relatively close to an address of the medical checkup target person is more likely to be selected as the recommended facility than the medical checkup facility that is relatively far from the address of the medical checkup target person. When the fourth rule is used, the recommended medical checkup information included in the facility presentation request inputted at the step S10 may include an information related to the address of the medical checkup target person. Alternatively, the facility selection unit 121 may obtain the information related to the address of the medical checkup target person separately from the facility presentation request. For example, when the storage apparatus 11 stores medical chart DB 112 (see FIG. 8 to FIG. 9) described later, the facility selection unit 121 may obtain the information related to the address of the medical checkup target person from the medical chart DB 112. As a result, the facility selection unit 121 is capable of selecting the recommended facility based on the information related to the address of the medical checkup facility included in the medical checkup facility information 1110 and the information related to the address of the medical checkup target person so that the fourth rule is satisfied. In this case, the facility selection unit 121 is capable of preferentially selecting, as the recommended facility, the medical checkup facility which the medical checkup target person is easily to visit. As a result, the convenience of the medical checkup target person is improved.

The facility selection unit 121 may further determine a date and time on which the recommended facility is capable of still accepting the new reservation for the recommended medical checkup from the medical checkup target person (in the below described description, it is referred to as a "reservation-ready date and time"). As described above, the facility detail information 1112 included in the medical checkup facility information 1110 includes the information related to the reservation status of the medical checkup that can be performed in the medical checkup facility. Thus, the facility selection unit 121 may further determine the reservation-ready date and time based on the medical checkup facility information 1110.

When the reservation-ready date and time is determined, the facility selection unit 121 may consider a date and time on which the medical checkup target person wants to take the recommended medical checkup. Namely, the facility selection unit 121 may determine the reservation-ready date and time within a range of the date and time on which the medical checkup target person wants to take the recommended medical checkup. In this case, it is preferable that the recommended medical checkup information included in the facility presentation request inputted at the step S10 include an information related to the date and time on which the medical checkup target person wants to take the recommended medical checkup. Alternatively, the facility selection unit 121 may obtain the information related to the date and time on which the medical checkup target person wants to take the recommended medical checkup separately from the facility presentation request.

Figure 7:
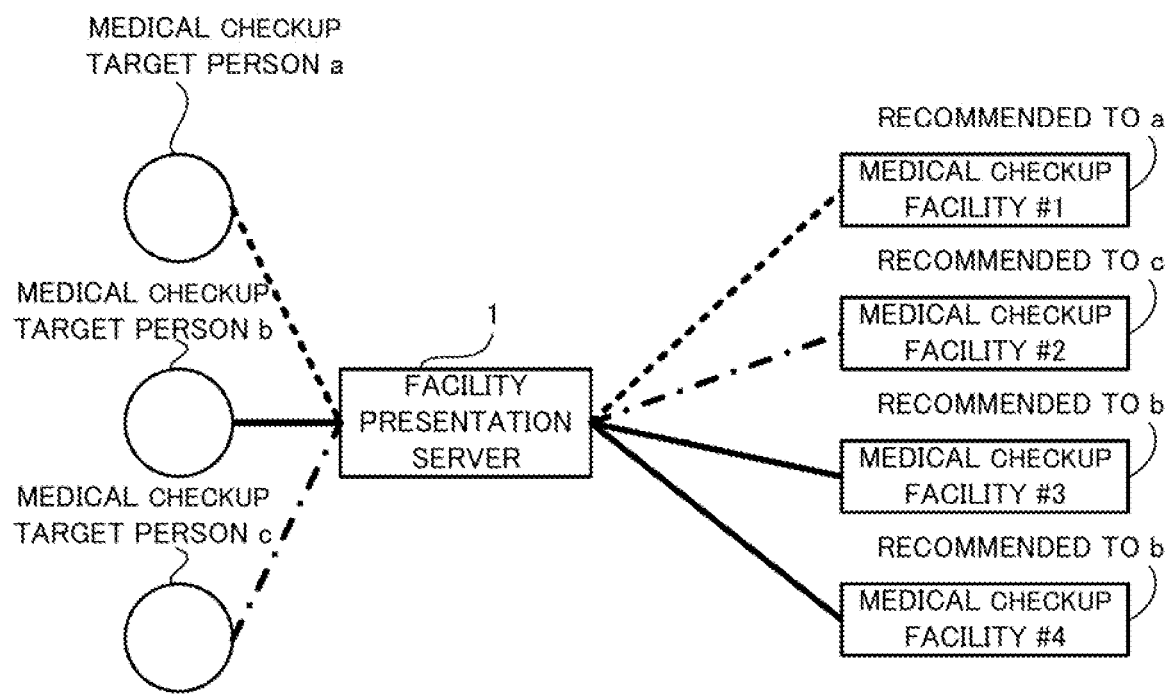
FIG. 7 conceptionally illustrates the operation for selecting the recommended facility.

When a plurality of medical checkup target persons intend to take the plurality of medical checkups, respectively, the facility selection unit 121 may select a plurality of recommended facilities corresponding to the plurality of medical checkup target persons, respectively, in parallel. Namely, when a plurality of facility presentation requests are inputted at the step S10 in FIG. 5, the facility selection unit 121 may select the plurality of recommended facilities in response to the plurality of facility presentation request, respectively, in parallel based on the plurality of recommended medical checkup information that are included in the plurality of facility presentation requests, respectively. Note that all of the plurality of medical checkups which the plurality of medical checkup target persons intend to take may be the same type of medical checkups. Alternatively, at least two of the plurality of medical checkups which the plurality of medical checkup target persons intend to take may be the different types of medical checkups. For example, FIG. 7 conceptionally illustrates a situation where recommended facilities are selected when the four medical checkup facilities #1 to #4 are the reservation-ready medical checkup facilities and each of a medical checkup target person a, a medical checkup target person b and a medical checkup target person c intends to take the recommended medical checkup. In an example illustrated in FIG. 7, the facility selection unit 121 selects the medical checkup facility #2 as the recommended facility for the medical checkup target person a, selects the medical checkup facilities #3 and #4 as the recommended facilities for the medical checkup target person b, and selects the medical checkup facility #1 as the recommended facility for the medical checkup target person c. In this case, an operation for selecting the plurality of recommended facilities corresponding to the plurality of medical checkup target persons may be regarded to be substantially equivalent to an operation for performing a matching between the plurality of medical checkup target persons and the plurality of recommended facilities. Note that all of the plurality of medical checkups which the plurality of medical checkup target persons intend to take may be the same type of medical checkups. Alternatively, at least two of the plurality of medical checkups which the plurality of medical checkup target persons intend to take may be the different types of medical checkups.

When same one medical checkup facility is selectable as the plurality of recommended facilities for the plurality of medical checkup target persons who intend to take the same type of recommended medical checkup, the facility selection unit 121 may select the same one medical checkup facility as the recommended facility for each of the plurality of medical checkup target persons. For example, in the example illustrated in FIG. 7, when the medical checkup target persons a and b intend to take the same type of medical checkup and the medical checkup facility #1 is selectable as the recommended facility for the medical checkup target person a and the recommended facility for the medical checkup target person b, the facility selection unit 121 may select the medical checkup facility #1 as each of the recommended facility for the medical checkup target person a and the recommended facility for the medical checkup target person b. Alternatively, in this case, the facility selection unit 121 may select one medical checkup facility as the recommended facility for at least one medical checkup target person and may not select the one medical checkup facility as the recommended facility for at least another medical checkup target person. For example, in the example illustrated in FIG. 7, when the medical checkup target persons a and b intend to take the same type of medical checkup and the medical checkup facility #1 is selectable as the recommended facility for the medical checkup target person a and the recommended facility for the medical checkup target person b, the facility selection unit 121 may select the medical checkup facility #1 as the recommended facility for the medical checkup target person a and may not select the medical checkup facility #1 as the recommended facility for the medical checkup target person b. In other words, the facility selection unit 121 may select one medical checkup facility as the recommended facility for at least one medical checkup target person and may select another medical checkup facility different from the one medical checkup facility as the recommended facility for at least another medical checkup target person. For example, in the example illustrated in FIG. 7, when the medical checkup target persons a and b intend to take the same type of medical checkup, the medical checkup facility #1 is selectable as the recommended facility for the medical checkup target person a and the recommended facility for the medical checkup target person b and the medical checkup facility #2 is selectable as the recommended facility for the medical checkup target person b, the facility selection unit 121 may select the medical checkup facility #1 as the recommended facility for the medical checkup target person a and may select the medical checkup facility #2 as the recommended facility for the medical checkup target person b.

In this case, the facility selection unit 121 may select the plurality of recommended facilities that corresponds to the plurality of medical checkup target persons, respectively, based on not only the recommended medical checkup information and the medical checkup facility DB 111 but also an information related to the plurality of medical checkup target persons. An information related to a history of the medical examination (namely, at least one of the medical consultation and the treatment) that has been taken by the medical checkup target person as the patient is one example of the information related to the medical checkup target person. In this case, as illustrated in FIG. 8, the storage apparatus 11 may store a medical chart DB 112 including the information related to the history of the medical examination that has been taken in the healthcare institution by the medical checkup target person.

The medical chart DB 112 is a database that stores medical chart data 1120 including the information related to the history of the medical examination that has been taken by the medical checkup target person as the patient. Generally, there are a plurality of patients who have taken the medical examination in the healthcare institution. Thus, the medical chart DB 112 typically stores a plurality of medical chart data 1120 that correspond to the plurality of patients (namely, the plurality of medical checkup target persons), respectively. Each medical chart data 1120 includes at least data related to a history of the medical examination that has been taken in the healthcare institution by one patient corresponding to each medical chart data 1120.

Figures 8, 9:
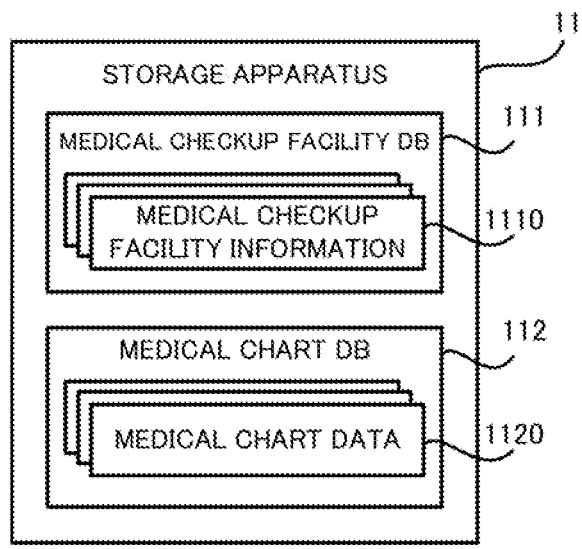
FIG. 8 is a block diagram that illustrates a storage apparatus storing a medical chart DB.
FIG. 9 is a data structure diagram that illustrates one example of a data structure of medical chart data.

FIG. 9 illustrates one example of the medical chart data 1120. As illustrated in FIG. 9, the medical chart data 1120 may include a patient basic information 1121 and a medical examination history information 1122.

The patient basic information 1121 includes an information related to the individual patient (typically, a personal information). For example, in an example illustrated in FIG. 9, the patient basic information 1121 includes a patient ID for identifying the patient, an information related to a name of the patient, an information related to an address of the patient, an information related to a body height of the patient, an information related to a body weight of the patient, and an information related to a past medical history (for example, at least one of a history of a disease, a history of a medication and a history of an allergy) of the patient. However, the patient basic information 1121 may not include at least one of plurality of these information. The patient basic information 1121 may include other information in addition to or instead of at least one of the plurality of information illustrated in FIG. 9. For example, the patient basic information 1121 may include at least one of an information related to a birth date of the patient, an information related to a phone number of the patient, an information related to a place of a work of the patient, an information related to an emergency contact number of the patient, an information of a social history of the patient, an information related to a family history of the patient (namely, a past medical history of a family or a housemate of the patient) and an information related to a genome sequence of the patient.

The medical examination history information 1122 includes an information related to the history of the medical examination (in other words, a process of the medical examination) that has been taken by the patient in the healthcare institution. For example, in the example illustrated in FIG. 9, the medical examination history information 1122 includes an information related to a chief compliant, an information related to a detail of the medical consultation by the doctor, an information related to a treatment policy decided by the doctor, an information related to a detail of the treatment provided by the doctor, an information related to a detail of a medicine prescribed by the doctor, an information related to a detail of an instruction from the doctor to the patient or the healthcare worker, an information related to an medical interview for the patient and an information related to the medical checkup that has been taken by the patient. However, the medical examination history information 1122 may not include at least one of the plurality of these information. The medical examination history information 1122 may include other information in addition to or instead of at least one of the plurality of information illustrated in FIG. 9. For example, the medical examination history information 1122 may include at least one of an information related to a history of an informed consent, an information related to an explanation and so on provided from the healthcare worker to the patient and an information related to a question and so on asked by the patient to the healthcare worker.

The medical chart data 1120 may include an information related to the history of the medical examination that has been taken by the patient in one healthcare institution for which the facility presentation server 1 is placed. The medical chart data 1120 may include an information related to the history of the medical examination that has been taken by the patient in another healthcare institution that is different from the one healthcare institution for which the facility presentation server 1 is placed. For example, the medical chart data 1120 may include an information related to the history of the medical examination that has been taken by the patient in another healthcare institution affiliated with (namely, having same affiliation with) one healthcare institution. Alternatively, the information related to the history of the medical examination that has been taken by the patient in another healthcare institution may be stored in a storage apparatus placed for another healthcare institution in a form that allows the facility presentation server 1 placed for one healthcare institution to use it. In this case, the facility presentation server 1 may download or use, through a communication network, the information stored in the storage apparatus placed for another healthcare institution.

Considering the information included in the medical chart data 1120, it can be said that the medical chart data 1120 includes an information related to a health condition of the medical checkup target person. In this case, the facility selection unit 121 may select the recommended facility so that a possibility that one medical checkup facility is selected as the recommended facility for one medical checkup target person whose health condition is relatively worse is higher than a possibility that the one medical checkup facility is selected as the recommended facility for another medical checkup target person whose health condition is relatively better, in a situation where the same one medical checkup facility is selectable as the recommended facility for each of the plurality of medical checkup target persons who intend to take same recommended medical checkup. Namely, the facility selection unit 121 may preferentially select the recommended facility for one medical checkup target person whose health condition is relatively worse. As one example, the facility selection unit 121 may select the recommended facility so that a possibility that one medical checkup facility is selected as the recommended facility for one medical checkup target person who has a relatively high risk to catch the disease that is expected to be assessed (in other words, that is expected to be checked) by the recommended medical checkup is higher than a possibility that the one medical checkup facility is selected as the recommended facility for another medical checkup target person who has a relatively low risk to catch the disease that is expected to be assessed by the recommended medical checkup. Namely, the facility selection unit 121 may preferentially select the recommended facility for one medical checkup target person who has a relatively high risk to catch the disease that is expected to be assessed by the recommended medical checkup.

Moreover, the facility selection unit 121 may preferentially select the recommended facility for one medical checkup target person whose health condition is relatively worse, even in a situation where the plurality of different medical checkup facilities are selectable as the recommended facility for each of the plurality of medical checkup target persons who intend to take same recommended medical checkup. For example, the facility selection unit 121 may preferentially select, as the recommended facility, one medical checkup facility of the plurality of medical checkup facilities that has a better medical checkup equipment for one medical checkup target person whose health condition is relatively worse, rather than for another medical checkup target person whose health condition is relatively better. Namely, there is one medical checkup facility of the plurality of medical checkup facilities that has the better medical checkup equipment, the facility selection unit 121 may prioritize selecting the one medical checkup facility as the recommended facility for one medical checkup target person whose health condition is relatively worse over selecting the one medical checkup facility as the recommended facility for another medical checkup target person whose health condition is relatively better. For example, the facility selection unit 121 may preferentially select, as the recommended facility, one medical checkup facility of the plurality of medical checkup facilities that can be reserved at the most recent date and time for one medical checkup target person whose health condition is relatively worse, rather than for another medical checkup target person whose health condition is relatively better. Namely, there is one medical checkup facility of the plurality of medical checkup facilities that can be reserved at the most recent date and time, the facility selection unit 121 may prioritize selecting the one medical checkup facility as the recommended facility for one medical checkup target person whose health condition is relatively worse over selecting the one medical checkup facility as the recommended facility for another medical checkup target person whose health condition is relatively better. In this case, the facility selection unit 121 may select, as the recommended facility, another medical checkup facility different from the one medical checkup facility for another medical checkup target person whose health condition is relatively better.

Alternatively, the facility selection unit 121 may use the medical chart data 1120 (for example, the information related to health condition of the medical checkup target person, even when the recommended facility for single medical checkup target person is selected. For example, the facility selection unit 121 may select, as the recommended facility, the medical checkup facility of the plurality of medical checkup facilities that has the better medical checkup equipment for the medical checkup target person whose health condition is relatively worse. For example, the facility selection unit 121 may select, as the recommended facility, the medical checkup facility of the plurality of medical checkup facilities that can be reserved at the most recent date and time for the medical checkup target person whose health condition is relatively worse. For example, the facility selection unit 121 may select, as the recommended facility, the medical checkup facility of the plurality of medical checkup facilities that is relatively large in size for the medical checkup target person whose health condition is relatively worse. For example, the facility selection unit 121 may select, as the recommended facility, the medical checkup facility of the plurality of medical checkup facilities that is not relatively large in size for the medical checkup target person whose health condition is relatively worse.

When the plurality of recommended facilities that correspond to the plurality of medical checkup target persons, respectively, are selected, the facility selection unit 121 may select the recommended facilities by using a machine learning model 124 that is configured to output the plurality of recommended facilities that correspond to the plurality of medical checkup target persons, respectively, when the information related to the plurality of recommended medical checkups which the plurality of medical checkup target persons intend to take, respectively, are inputted thereto. Note that the machine learning model may be a machine learning model using a Neural Network, for example. In this case, it is preferable to perform a learning operation for setting a parameter of the machine learning model (for example, at least one of a weight and a bias of the Neural Network) by learning data, before the facility selection unit 121 selects the recommended facility by using the machine learning model. The learning data may include data corresponding to the plurality of medical checkup facility information 1110 stored in the medical checkup facility DB 111. The learning data may include data corresponding to the information related to the plurality of *medica* test target persons (for example, the medical chart data 1120). The learning data may include data corresponding to the recommended medical checkup information. For example, the learning operation may be an operation for setting the parameter of the machine learning model so that a difference between the information related to the recommended facility outputted from the machine learning model when at least the learning data is inputted into the machine learning model and a ground truth (namely, a ground truth information of the medical checkup facility that is desired to be selected as the recommended facility) that is generated in association with the learning data is smaller. Incidentally, the facility selection unit 121 may select the recommended facility for single medical checkup target person by using the machine learning model, not only in the case where the even when the plurality of recommended facilities that correspond to the plurality of medical checkup target persons, respectively, are selected. Namely, the facility selection unit 121 may select the recommended facility by using the machine learning model in addition to or instead of the above described rule-based selection engine.

Figures 10, 11:
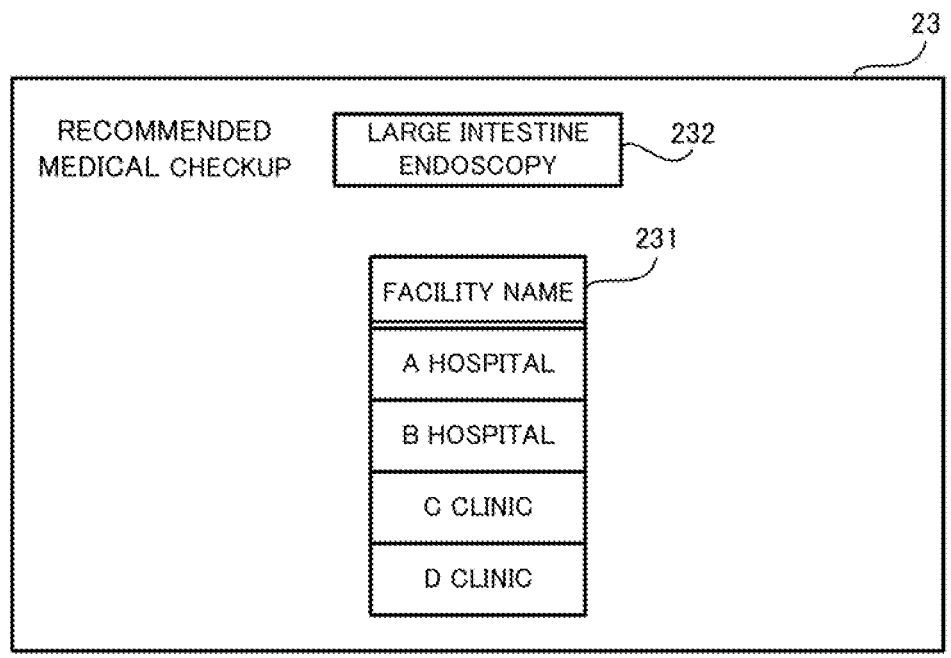
FIG. 10 illustrates one example of a recommended facility information that is presented to a presentation target person.
FIG. 11 illustrates one example of the recommended facility information that is presented to the presentation target person.

Again in FIG. 5, then, the facility presentation unit 122 controls the information terminal 2 to present, to the presentation target person, the recommended facility information related to the recommended facility selected by the facility selection unit 121 at the step S12 (a step S13). As a result, the information terminal 2 outputs, by using the output apparatus 23, the recommended facility information in the form that allows the presentation target person to recognize it. For example, when the output apparatus 23 is the display apparatus, the output apparatus 23 may display, as the recommended facility information, a GUI (Graphical User Interface) including a display field 231 indicating the name of the recommended facility, as illustrated in FIG. 10 that illustrates one example of the recommended facility information presented to the presentation target person. FIG. 10 illustrate one example of the recommended facility information that is displayed when each of a A hospital, a B hospital, a C clinic and a D clinic are selected as the recommended facility. Incidentally, the facility presentation unit 122 may present, to the presentation target person, the recommended facility information including an item name of the recommended medical checkup as illustrated in FIG. 10, in order to allow the presentation target person to recognize the recommended medical checkup that is recommended to be taken in the presented recommended facility. For example, the output apparatus 23 may display, as a part of the recommended facility information, a GUI including a display field 232 indicating the item name of the recommended *medica* test, under the control of the facility presentation unit 122.

When the facility selection unit 121 determines the date and time on which the recommended facility is capable of still accepting the new reservation for the recommended medical checkup from the medical checkup target person (namely, the reservation-ready date and time) as described above, the facility presentation unit 122 may control the information terminal 2 to present, to the presentation target person, the recommended facility information indicating not only the name of the recommended facility but also the reservation-ready date and time. As a result, the convenience of the medical presentation target person is improved. For example, as illustrated in FIG. 11 that illustrates another example of the recommended facility information presented to the presentation target person, the output apparatus 23 may display, as a part of the recommended facility information, a GUI including a display field 233 indicating the reservation-ready date and time, under the control of the facility presentation unit 122. In this case, the output apparatus 23 may display, as a part of the recommended facility information, the GUI including the display field 233 indicating an availability of the recommended facility on the reservation-ready date and time. In an example illustrated in FIG. 11, the availability of the recommended facility is displayed by using a symbol "○" that represents that the number of the new reservation for the medical checkup that can be still accepted by the recommended facility is relatively large, a symbol "Δ" that represents that the number oft the new reservation for the medical checkup that can be still accepted by the recommended facility is relatively small, a symbol "x" that represents that the new reservation for the medical checkup cannot be accepted by the recommended facility, and a numerical number that indicate, when the number of the new reservation for the medical checkup that can be still accepted by the recommended facility is equal to or smaller than a predetermined number, this number. Note that the number of the new reservation for the medical checkup that can be still accepted by the recommended facility may be displayed even when the number of the new reservation for the medical checkup that can be still accepted by the recommended facility is not equal to or smaller than the predetermined number. The number of the new reservation for the medical checkup that can be still accepted by the recommended facility may be displayed together with at least one of the symbol "○", the symbol "Δ" and the symbol "x". Moreover, in order to allow the presentation target person recognizing the recommended facility information to reserve the recommended facility promptly, the output apparatus 23 may embed a hyperlink, which is connected to a reservation screen for the recommended facility in response to a click, in the display field 233 that indicates the number of the new reservation for the medical checkup that can be still accepted by the recommended facility. As a result, the convenience of the medical checkup target person is improved. Moreover, when the date and time on which the medical checkup target person wants to take the recommended medical checkup is considered to determine the reservation-ready date and time as described above, he output apparatus 23 may display, as a part of the recommended facility information, a GUI including a display field 234 indicating the date and time on which the medical checkup target person wants to take the recommended medical checkup, under the control of the facility presentation unit 122.

(3) Technical Effect of Facility Presentation System SYS

As described above, the facility presentation server 1 in the present example embodiment is capable of properly selecting the recommended facility in which the medical checkup target person is recommended to take the recommended medical checkup and presenting it to the presentation target person. Especially, the facility presentation server 1 is capable of selecting, as the recommended facility, at least one medical checkup facility that is suitable for the medical checkup target person from the plurality of medical checkup facilities based on the plurality of medical checkup facility information 1110 including the information related to the plurality of medical checkup facilities, respectively. Thus, the facility presentation server 1 is capable of properly selecting the recommended facility that considers a status of the medical checkup facility and/or that is more suitable for the medical checkup target person, compared to a case where the recommended facility is selected without using the medical checkup facility information 1110. For example, the facility presentation server 1 is capable of selecting the recommended facility to satisfy a requirement of the medical checkup target person to take the recommended medical checkup in the proper medical checkup facility. For example, as described above, the facility presentation server 1 is capable of selecting the recommended facility to effectively use the resource of the plurality of medical checkup facilities. Namely, the facility presentation server 1 is capable of selecting the recommended facility to satisfy a requirement of the healthcare institution to effectively use the resource of the plurality of medical checkup facilities.

(4) Modified Example of Facility Presentation System SYS

Figure 12:
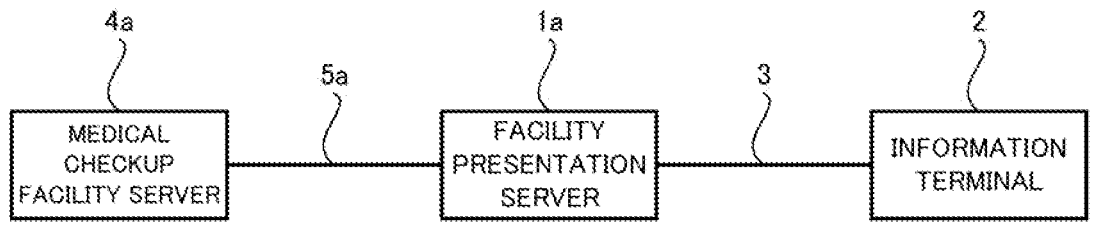
FIG. 12 is a block diagram that illustrates an entire configuration of a facility presentation system in a modified example.

Next, with reference to FIG. 12, a modified example of the facility presentation system SYS (in the below described description, the facility presentation system SYS in the modified example is referred to as a "facility presentation system SYSa") will be described. FIG. 12 is a block diagram that illustrates an entire configuration of the facility presentation system SYSa in the modified example.

As illustrated in FIG. 12, the facility presentation system SYSa is different from the above described facility presentation system SYS in that it may further include a medical checkup facility server 4a. Furthermore, the facility presentation system SYSa is different from the above described facility presentation system SYS in that it includes a facility presentation server 1a instead of the facility presentation server 1. Another feature of the facility presentation system SYSa may be same as another feature of the facility presentation system SYS.

The medical checkup facility server 4a is an information processing apparatus that is usable by the medical checkup facility. Thus, the medical checkup facility server 4a is typically placed for the medical checkup facility. When there are the plurality of medical checkup facilities as described above, a plurality of medical checkup facility servers 4a may be placed for the plurality of medical checkup facilities, respectively. The medical checkup facility server 4a is configured to communicate with the facility presentation server 1a through a communication network 5a. The communication network 5a may include a wired communication network and may include a wireless communication network.

Figure 13:
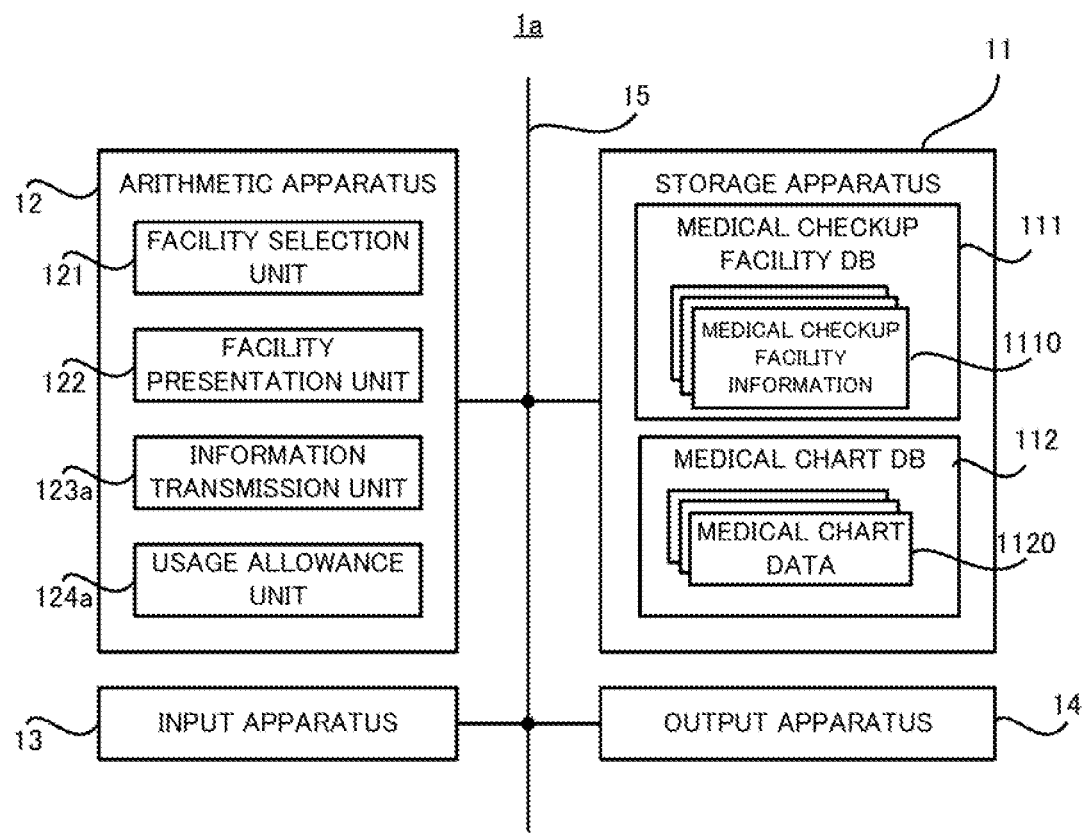
FIG. 13 is a block diagram that illustrates a configuration of a facility presentation server in the modified example.

A configuration of the facility presentation server 1a in the modified example is illustrated in FIG. 13. As illustrated in FIG. 13, the facility presentation server 1a is different from the above described facility presentation server 1 in that it further includes an information transmission unit 123a that is one specific example of a "transmission unit" and a usage allowance unit 124a that is one specific example of an "allowance unit" logical functional blocks implemented in the arithmetic apparatus 12. Furthermore, the facility presentation server 1a is different from the above described facility presentation server 1 in that the storage apparatus 11 store the medical chart DB 112 (see FIG. 8 to FIG. 9). Another feature of the facility presentation server 1a may be same as another feature of the facility presentation server 1.

When one recommended facility is designated as the medical checkup facility in which the medical checkup target person actually takes the recommended medical checkup, the information transmission unit 123a is configured to notify the designated one recommended facility (in the below described description, it is referred to as a "designated facility") of that fact. Specifically, the information transmission unit 123a is configured to transmit, to the medical checkup facility server 4a of the designated facility through the communication network 5a, a notification information for notifying the designated facility of the information related to the medical checkup target person. The notification information may include an information indicating the medical checkup target person (for example, an information indicating a name of the medical checkup target person), for example. The notification information may include an information indicating recommended medical checkup that is expected to be taken by the medical checkup target person (for example, an information indicating he item name of the recommended medical checkup), for example. The notification information may include an information indicating the date and time on which the medical checkup target person wants to take the recommended medical checkup (alternatively, a reserved date and time when the medical checkup target person has already reserved the designated facility by using the recommended facility information outputted from the output apparatus 23), for example. The notification information may include an information indicating the healthcare institution for which the facility presentation server 1 is placed (namely, the healthcare institution that refers the medical checkup target person to the designated facility) (for example, an information indicating a name of the healthcare institution), for example. The notification information may include an information indicating the designated facility (for example, the name of the designated facility), for example.

The notification information may be used as an information corresponding to a patient referral document (what we call a reference letter) that is generally used in the healthcare institution. Thus, the notification information may include an information described in the patient referral document (what we call the reference letter).

The notification information may be send to the designated facility as a document on which a content of the notification information is printed. In this case, the facility server 1a may issue the document on which the content of the notification information is printed by using at least one of the output apparatus 14 and the output apparatus 23 of the information terminal 2 that are configured to serve as a printing apparatus (what we call a printer). Namely, the content of the notification information may be transmitted from the arithmetic apparatus 12 to the output apparatus 14 or the output apparatus 23 of the information terminal 2 (alternatively, another output apparatus) in a printable form. The document on which the content of the notification information is printed in this manner may be used as the patient referral document (what we call the reference letter).

When the notification information is transmitted from the facility presentation server 1a to the medical checkup facility server 4a, a person in charge in the designated facility can recognize relatively easily what medical checkup target person intends to take what type of medical checkup.

The usage allowance unit 124a is configured to allow the designated facility to use the medical chart data 1120 of the medical checkup target person. For example, the usage allowance unit 124a may transmit the medical chart data 1120 of the medical checkup target person stored in the storage apparatus 11 to the medical checkup facility server 4a of the designated facility through the communication network 5a. Alternatively, for example, the usage allowance unit 124a may allow the medical checkup facility server 4a of the designated facility to access (namely, refer) the medical chart data 1120 of the medical checkup target person stored in the storage apparatus 11. In this case, the medical checkup facility server 4a may access the medical chart data 1120 of the medical checkup target person stored in the storage apparatus 11 through the communication network 5a. As one example, the medical checkup facility server 4a may access (for example, obtain, browse or use) the medical chart data 1120 of the medical checkup target person by using an API (Application Program Interface) designated by the facility presentation server 1a (alternatively, the healthcare institution using the facility presentation server 1a).

When the designated facility is allowed to use the medical chart data 1120 in this manner, the person in charge in the designated facility can recognize the condition (for example, the health condition) of the medical checkup target person. Thus, the person in charge in the designated facility may not conduct, in the designated facility, the medical interview that is unnecessary to recognize the condition of the medical checkup target person (for example, the medical interview that is same as the medical interview the result of which is already included in the medical chart data 1120). Alternatively, the person in charge in the designated facility can recognize the condition of the medical checkup target person before the medical checkup target person actually visits the designated facility to take the recommended medical checkup. Thus, the person in charge in the designated facility can prepare the recommended medical checkup based on the condition of the medical checkup target person that is recognized in advance.

The usage allowance unit 124a may allow the designated facility to use the medical chart data 1120 on a condition that the medical checkup target person agrees that the designated facility uses the medical chart data 1120. Namely, the usage allowance unit 124a may not allow the designated facility to use the medical chart data 1120 when the medical checkup target person does not agree that the designated facility uses the medical chart data 1120. In other words, the usage allowance unit 124a may prohibit the designated facility from using the medical chart data 1120 when the medical checkup target person does not agree that the designated facility uses the medical chart data 1120.

In order to obtain an agreement of the medical checkup target person, the facility presentation unit 122 may control the information terminal 2 (especially, the output apparatus 23) to present, to the presentation target person (in this case, the medical checkup target person), an information for obtaining the agreement of the medical checkup target person in presenting the recommended facility information. For example, when the output apparatus 23 is the display apparatus, the output apparatus 23 may display a GUI 235a that is operable by the medical checkup target person to obtain the agreement of the medical checkup target person, as illustrated in FIG. 13 that illustrates one example of the recommended facility information presented to the presentation target person. In an example illustrated in FIG. 13, the GUI 235a includes a button that is pressed by the medical checkup target person when the medical checkup target person agrees that the designated facility uses the medical chart data 1120, and a button that is pressed by the medical checkup target person when the medical checkup target person does not agree that the designated facility uses the medical chart data 1120.

When the designated facility is allowed to use the medical chart data 1120 on the condition that the medical checkup target person agrees that the designated facility uses the medical chart data 1120 in this manner, it is possible to prevent an undesired leakage of the personal information (in this case, the medical chart data 1120) of the medical checkup target person.

The usage allowance unit 124a may change a range (for example, at least one of an amount of an information and a type of an information) of the medical chart data 1120 of the medical checkup target person which the designated facility is allowed to use. For example, the usage allowance unit 124a may change the range of the medical chart data 1120 of the medical checkup target person which the designated facility is allowed to use so that the range of the medical chart data 1120 of the medical checkup target person which the designated facility not affiliated with the healthcare institution using the facility presentation server 1a is allowed to use is narrower than the range of the medical chart data 1120 of the medical checkup target person which the designated facility affiliated with the healthcare institution using the facility presentation server 1a is allowed to use.

(5) Supplementary Note

With respect to the example embodiments described above, the following Supplementary Notes will be further disclosed.

[Supplementary Note 1]
A facility presentation apparatus including:
a selection unit that is configured to select, as a recommended facility, at least one medical checkup facility that is recommended to a medical checkup target person from a plurality of medical checkup facilities based on a medical checkup information indicating a medical checkup that is related to a healthcare and that is intended to be taken by the medical checkup target person, a medical checkup facility information related to the plurality of medical checkup facilities in each of which the medical checkup can be performed and medical chart data of the medical checkup target person; and
a presentation unit that is configured to present, to a presentation target person, a recommended facility information related to the recommended facility.

[Supplementary Note 2]
The facility presentation apparatus according to Supplementary Note 1, wherein
the selection unit is configured to select a plurality of recommended facilities that are recommended to a plurality of medical checkup target persons, respectively, based on the medical checkup information indicating a plurality of medical checkups that are intended to be taken by the plurality of medical checkup target persons, respectively, the medical checkup facility information and the medical chart data.

[Supplementary Note 3]
The facility presentation apparatus according to Supplementary Note 1 or 2, wherein
when a first medical checkup target person and a second medical checkup target person intend to take same medical checkup, the selection unit is configured to select, based on a state information related to a health condition of the medical checkup target person included in the medical chart data, the recommended facility for one medical checkup target person of the first and second medical target persons whose health condition is relatively worse more preferentially than other medical checkup target person of the first and second medical checkup target persons.

[Supplementary Note 4]
The facility presentation apparatus according to any one of Supplementary Notes 1 to 3 further including a transmission unit that is configured to transmit an information related to the medical checkup target person to the recommended facility.

[Supplementary Note 5]
The facility presentation apparatus according to any one of Supplementary Notes 1 to 4 further including a printed paper output unit that is configured to output a paper on which an information related to the medical checkup target person is printed.

[Supplementary Note 6]
The facility presentation apparatus according to any one of Supplementary Notes 1 to 5 further including an allowance unit that is configured to allow the recommended facility to use the medical chart data.

[Supplementary Note 7]
The facility presentation apparatus according to Supplementary Note 6, wherein
the allowance unit is configured to allow the recommended facility to use the medical chart data on a condition that the medical checkup target person agrees with a usage of the medical chart data by the recommended facility.

[Supplementary Note 8]
A facility presentation method including:
selecting, as a recommended facility, at least one medical checkup facility that is recommended to a medical checkup target person from a plurality of medical checkup facilities based on a medical checkup information indicating a medical checkup that is related to a healthcare and that is intended to be taken by the medical checkup target person, a medical checkup facility information related to the plurality of medical checkup facilities in each of which the medical checkup can be performed and medical chart data of the medical checkup target person; and
presenting, to a presentation target person, a recommended facility information related to the recommended facility.

[Supplementary Note 9]
A recording medium on which a computer program that allows a computer to execute:
a selection step at which at least one medical checkup facility that is recommended to a medical checkup target person is selected as a recommended facility from a plurality of medical checkup facilities based on a medical checkup information indicating a medical checkup that is related to a healthcare and that is intended to be taken by the medical checkup target person, a medical checkup facility information related to the plurality of medical checkup facilities in each of which the medical checkup can be performed and medical chart data of the medical checkup target person; and
a presentation step at which a recommended facility information related to the recommended facility is presented to a presentation target person,
is recorded.

[Supplementary Note 10]
A computer program that allows a computer to execute:
a selection step at which at least one medical checkup facility that is recommended to a medical checkup target person is selected as a recommended facility from a plurality of medical checkup facilities based on a medical checkup information indicating a medical checkup that is related to a healthcare and that is intended to be taken by the medical checkup target person, a medical checkup facility information related to the plurality of medical checkup facilities in each of which the medical checkup can be performed and medical chart data of the medical checkup target person; and
a presentation step at which a recommended facility information related to the recommended facility is presented to a presentation target person.

This disclosure is not limited to the above described example embodiment. This disclosure is allowed to be changed, if desired, without departing from the essence or spirit of the invention which can be read from the claims and the entire specification, and a facility presentation apparatus, a facility presentation method and a recording medium, which involve such changes, are also intended to be within the technical scope of this disclosure.

This application is based upon and claims the benefit of priority from Japanese Patent Application No. 2020-097593, filed on Jun. 4, 2020, and incorporates all of its disclosure herein. Moreover, this application incorporates all of the publications of application and articles.

DESCRIPTION OF REFERENCE CODES

SYS facility presentation system
1 facility presentation server
11 storage apparatus
111 test facility DB
1110 test facility data
1111 facility basic information
1112 facility detail information
112 medical chart DB
1120 medical chart data
1121 patient basic information
1122 medical examination history information
12 arithmetic apparatus
121 facility selection unit
122 facility presentation unit
2 information terminal
22 arithmetic apparatus
23 output apparatus

What is claimed is:

1. A facility presentation apparatus comprising:
at least one memory storing instructions; and
at least one processor configured to execute the instructions to:
determine a recommended medical checkup and a reservation-ready date and time when a facility presentation request is input from a user through a user interface;
allow a model learned by using machine learning to output recommended facility information for supporting decision-making of the user related to a recommended facility by inputting information about the recommended medical checkup, wherein the recommended facility information includes at least a name of the recommended facility;
display a user interface including a display field indicating a name of the recommended facility the a display field indicating the reservation-ready date and time for the recommended facility, the user interface operable by a medical checkup target person to obtain agreement of a medical checkup target person on use of medical chart data of the medical checkup target person by the recommended facility;
notify a designated facility that the medical checkup target person will take the recommended medical checkup when the user designates one recommended facility as the designated facility where the medical checkup target person will take the recommended medical checkup, through the user interface; and
allow at least one of transmission of the medical chart data to the designated facility through a communication network and access to the medical chart data using an API (Application Program Interface) by the designated facility, when the medical checkup target person agrees to the use of the medical chart data by the designated facility, wherein
the model learned by using machine learning is set with at least one of a weight and a bias of a neural network so as to reduce an error between the recommended facility information output when learning data is input and ground truth information,
the learning data includes
medical checkup information indicating a medical checkup that is related to healthcare and that is intended to be performed on the medical checkup target person,
medical checkup facility information related to a plurality of medical checkup facilities at each of which the recommended medical checkup can be performed,
and the medical chart data, and
the ground truth information is information regarding the medical checkup facility that is desired to be selected as the recommended facility, and is generated in association with the learning data.

2. The facility presentation apparatus according to claim 1, wherein
the at least one processor is configured to execute the instructions to respectively select a plurality of recommended facilities that are recommended to a plurality of medical checkup target persons, based on the medical checkup information indicating a plurality of medical checkups that are intended be respectively taken by the plurality of medical checkup target persons, the medical checkup facility information, and the medical chart data.

3. The facility presentation apparatus according to claim 1, wherein
when a first medical checkup target person and a second medical checkup target person intend to take a same medical checkup, the at least one processor is configured to execute the instructions to select, based on state information related to a health condition of the medical checkup target person included in the medical chart data, the recommended facility for one medical checkup target person of the first and second medical target persons of which the health condition is worse more preferentially than another medical checkup target person of the first and second medical checkup target persons.

4. The facility presentation apparatus according to claim 1, wherein
the at least one processor is configured to execute the instructions to transmit information related to the medical checkup target person to the recommended facility.

5. The facility presentation apparatus according to claim 1 further comprising a printer that is configured to output paper on which information related to the medical checkup target person is printed.

6. The facility presentation apparatus according to claim 1, wherein
the at least one processor is configured to execute the instructions to allow the recommended facility to use the medical chart data.

7. The facility presentation apparatus according to claim 6, wherein
the at least one processor is configured to execute the instructions to allow the recommended facility to use the medical chart data on a condition that the medical checkup target person agrees with the use of the medical chart data by the recommended facility.

8. A facility presentation method performed by a computer and comprising:
determining a recommended medical checkup and a reservation-ready date and time when a facility presentation request is input from a user through a user interface;
allowing a model learned by using machine learning to output recommended facility information for supporting decision-making of the user related to a recommended facility by inputting information about the recommended medical checkup, wherein the recommended facility information includes at least a name of the recommended facility;

displaying a user interface including a display field indicating a name of the recommended facility the a display field indicating the reservation-ready date and time for the recommended facility, the user interface operable by a medical checkup target person to obtain agreement of a medical checkup target person on use of medical chart data of the medical checkup target person by the recommended facility;

notifying a designated facility that the medical checkup target person will take the recommended medical checkup when the user designates one recommended facility as the designated facility where the medical checkup target person will take the recommended medical checkup, through the user interface; and allowing at least one of transmission of the medical chart data to the designated facility through a communication network and access to the medical chart data using an API (Application Program Interface) by the designated facility, when the medical checkup target person agrees to the use of the medical chart data by the designated facility, wherein the model learned by using machine learning is set with at least one of a weight and a bias of a neural network so as to reduce an error between the recommended facility information output when learning data is input and ground truth information, the learning data includes
- medical checkup information indicating a medical checkup that is related to healthcare and that is intended to be performed on the medical checkup target person,
- medical checkup facility information related to a plurality of medical checkup facilities at each of which the recommended medical checkup can be performed,
- and the medical chart data, and the ground truth information is information regarding the medical checkup facility that is desired to be selected as the recommended facility, and is generated in association with the learning data.

9. A non-transitory recording medium a computer program executable by a computer to perform processing comprising:

determining a recommended medical checkup and a reservation-ready date and time when a facility presentation request is input from a user through a user interface;

allowing a model learned by using machine learning to output recommended facility information for supporting decision-making of the user related to a recommended facility by inputting information about the recommended medical checkup, wherein the recommended facility information includes at least a name of the recommended facility;

displaying a user interface including a display field indicating a name of the recommended facility the a display field indicating the reservation-ready date and time for the recommended facility, the user interface operable by a medical checkup target person to obtain agreement of a medical checkup target person on use of medical chart data of the medical checkup target person by the recommended facility;

notifying a designated facility that the medical checkup target person will take the recommended medical checkup when the user designates one recommended facility as the designated facility where the medical checkup target person will take the recommended medical checkup, through the user interface; and allowing at least one of transmission of the medical chart data to the designated facility through a communication network and access to the medical chart data using an API (Application Program Interface) by the designated facility, when the medical checkup target person agrees to the use of the medical chart data by the designated facility, wherein the model learned by using machine learning is set with at least one of a weight and a bias of a neural network so as to reduce an error between the recommended facility information output when learning data is input and ground truth information, the learning data includes
- medical checkup information indicating a medical checkup that is related to healthcare and that is intended to be performed on the medical checkup target person,
- medical checkup facility information related to a plurality of medical checkup facilities at each of which the recommended medical checkup can be performed,
- and the medical chart data, and the ground truth information is information regarding the medical checkup facility that is desired to be selected as the recommended facility, and is generated in association with the learning data.

* * * * *